United States Patent [19]

Affeldt et al.

[11] 4,112,929
[45] Sep. 12, 1978

[54] METHOD FOR MEASURING THE BLOOD PRESSURE OF A PATIENT

[75] Inventors: Karl-Heinz Affeldt; Günther Fritzsche; Joachim Ganzke; Gerhard Raupach, all of Berlin, Fed. Rep. of Germany

[73] Assignee: Robert Bosch GmbH, Stuttgart, Fed. Rep. of Germany

[21] Appl. No.: 812,402

[22] Filed: Jul. 1, 1977

[51] Int. Cl.² .............................................. A61B 5/02
[52] U.S. Cl. .......................... 128/2.05 M; 128/2.05 A
[58] Field of Search ...................... 128/2.05 A, 2.05 G, 128/2.05 M, 2.05 Q

[56] References Cited

U.S. PATENT DOCUMENTS

| 2,352,875 | 7/1944 | Williams et al. | 128/2.05 A |
| 3,056,401 | 10/1962 | Greenspan et al. | 128/2.05 G |
| 3,117,570 | 1/1964 | Halasz et al. | 128/2.05 M |

FOREIGN PATENT DOCUMENTS

| 869,032 | 4/1971 | Canada | 128/2.05 A |

Primary Examiner—Robert W. Michell
Assistant Examiner—Francis J. Jaworski
Attorney, Agent, or Firm—Spencer & Kaye

[57] ABSTRACT

A blood pressure measuring procedure which can be performed by the subject employing a manually inflatable cuff and associated microphone, a measuring circuit responsive to signals having the form of Korotkoff sounds, a dual-indicator manometer having two individually controllable indicators, a control circuit for controlling the operation of the indicators, and a switch switchable between a pumping position in which it permits the cuff to be manually inflated and releases the indicators to respond to the cuff pressure and a measuring position in which the cuff pressure gradually decreases, one indicator is locked in its present position at the onset of Korotkoff sound signals and the other indicator is locked in its present position upon termination of Korotkoff sound signals. The subject places the cuff in position, moves the switch to its pumping position, inflates the cuff to a pressure above his systolic pressure, and then moves the switch to its measuring position.

14 Claims, 3 Drawing Figures

METHOD FOR MEASURING THE BLOOD PRESSURE OF A PATIENT

BACKGROUND OF THE INVENTION

The present invention relates to measurement of the blood pressure of a patient.

The invention relates particularly to a procedure which is based on the method of Riva-Rocci/Korotkoff, and in which the patient himself secures an inflatable pressure cuff in place and switches a switch into a first switch position to automatically close a valve, subsequent opening of the valve after the cuff has been inflated permitting the air in the cuff to slowly escape. Simultaneously a battery-fed current supply circuit is switched on, two indicators of a dual indicator manometer, which are blocked when the current supply circuit is switched off, are released by exciting respective electromagnets, and an electronic barrier is switched on to prevent blocking of the indicators. Thereafter the patient pumps the cuff to a pressure which lies above his systolic blood pressure and switches the switch into a second switch position to open the valve, and an electrical device detects the start or stop, respectively, of the Korotkoff noise and blocks, at the respective start or stop, one of the indicators of the manometer. Blocking is effected by interrupting the circuit for one of the electromagnets. The electrical device also switches off the electrical circuit after both indicators have been blocked.

The present invention is based on a blood pressure measuring method in which the inflatable blood pressure cuff initially exerts, on an artery, a pressure above the patient's systolic pressure value, the cuff pressure is then gradually reduced and electrical signals are derived from the resulting Korotkoff sounds, a first indicator of a dual-indicator manometer which is influenced by the cuff pressure is blocked at the commencement of such signals, which occurs at the systolic pressure value, and the second indicator of the manometer is blocked upon termination of such signals, this occurring at the diastolic pressure value.

A sphygmomanometer which has a separate automatic indication for the systolic and diastolic pressure values is disclosed in German Offenlegungsschrift [Laid-open Application] No. DT-OS 22 09 633, which gives no precise information about the circuitry of the sphygmomanometer. Moreover, this sphygmomanometer has a relatively high current consumption and that publication provides no indication as to how this current consumption could be reduced.

Furthermore, U.S. Pat. No. 3,056,401 discloses a self-recording sphygmomanometer which has substantially the same drawbacks, although in this device no current is consumed when the indicators of the dual indicator manometer are blocked.

SUMMARY OF THE INVENTION

It is an object of the present invention to simplify the procedure required to obtain a blood pressure measurement.

Another object of the invention is to provide a simple apparatus and procedure which can be utilized by the subject himself.

A further object of the invention is to reduce the electrical power consumed by such apparatus.

These and other objects according to the invention are achieved by placing the cuff in position, moving a two-position switch into a pumping position which prevents deflation of the cuff and unblocks the manometer indicators, pumping the cuff to a pressure above the systolic pressure of the subject, and moving the switch into a measuring position which allows the pressure in the cuff to gradually decrease, one indicator to be blocked at the onset of Korotkoff sound signals, and the other indicator to be blocked at termination of the Korotkoff sound signals.

The system further includes an electrical power supply source which is connected when the switch is moved to its pumping position and disconnected after the switch has been moved to its measuring position and both indicators have become locked.

In accordance with a further feature of the invention, the apparatus is provided with a function indicator device including an indicator element which is switched on in the pumping position of the switch, remains on in the measuring position, and is switched off by the automatic switching off of the current supply circuit. Switching on of the indicator element indicates to the patient that he may begin to pump up the cuff and switching off of the indicator element indicates that the measurement is completed and the patient may remove the cuff.

DESCRIPTION OF THE PREFERRED EMBODIMENTS

Figure 1:
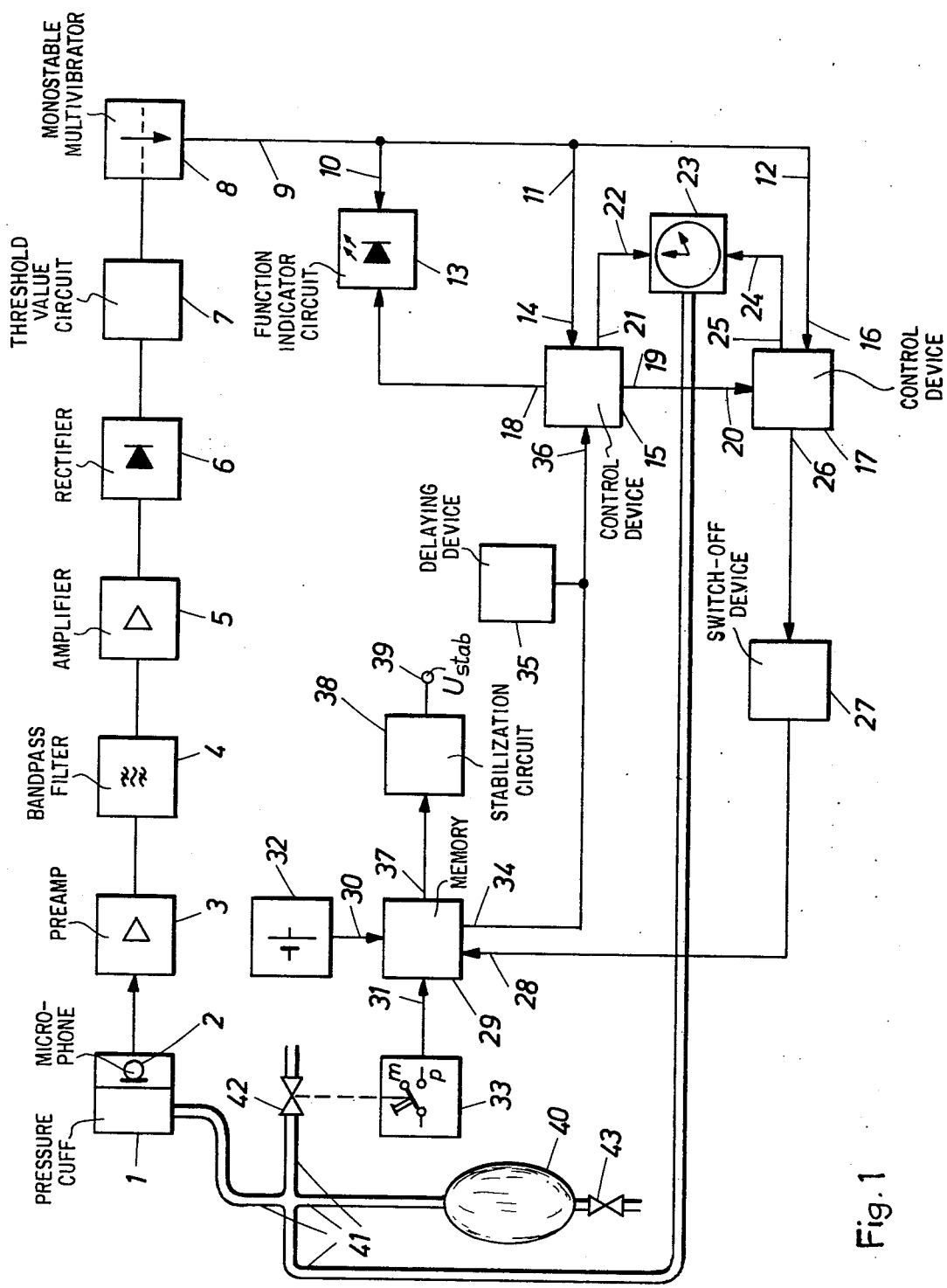
FIG. 1 is a block circuit diagram of one preferred embodiment of the invention.

In the system shown in FIG. 1, an inflatable pressure cuff 1 contains a microphone 2 which is preferably a body sound microphone. The body sound microphone is connected to a series-connected circuit path including a preamplifier 3, a bandpass filter 4 which essentially permits only the frequencies of the Korotkoff sound to pass, a postamplifier 5, a rectifier circuit 6, a threshold value circuit 7 and a monostable multivibrator 8. Three lines 10, 11 and 12 branch off from an output line 9 of the monostable multivibrator 8, the first line 10 being connected with a first input of a function indicator circuit 13, the second line 11 being connected with a first input 14 of a first control device 15 and the third line 12 being connected with a first input 16 of a second control device 17.

Control device 15 has a first output 18 connected to a second input of the function indicator circuit 13, a second output 19 connected to a second input 20 of the second control device 17, and a third output 21 connected to a first input 22 of a dual-indicator manometer 23. The second input 24 of manometer 23 is connected to a first output 25 of the second control device 17.

A second output 26 of the second control device 17 is connected to the input of a switch-off device 27 to automatically switch off the current supply circuit. The output of the switch-off device 27 is connected to a first input 28 of an electronic switch-on memory 29 which has three inputs 28, 30 and 31. The second input 30 of memory 29 is connected to a direct voltage source 32, preferably a battery, and the third input 31 is connected to a switch 33. Switch 33 has two switching positions, a measuring position $m$ and a pumping position $p$.

The switch-on memory 29 has a first output 34 connected in parallel with a delaying device 35 and to a second input 36 of the first control device 15, and a second output 37 connected to a stabilization circuit 38 provided for stabilizing the voltage from direct voltage source 32. A stabilized direct voltage $U_{stab}$ is available at an output 39 of the stabilization circuit to supply the system with operating current.

A squeeze bulb 40 provided to pump up cuff 1 is in communication, via air hoses 41, firstly with cuff 1, secondly with the dual-indicator manometer 23, and thirdly with a valve 42 which is mechanically coupled to switch 33. Bulb 40 is provided with a manually actuatable outlet valve 43 to enable air to be completely exhausted from the cuff after a blood pressure measurement.

The above-described device operates as follows: If a patient intends to measure his own blood pressure, he initially applies the pressure cuff 1, which is preferably of a type that can be secured in place with but one hand, taking care that the body sound microphone contained in the pressure cuff is placed approximately above one of the patient's arteries.

Thereupon the patient switches switch 33, which is preferably a rocker switch, into the pumping position $p$. This closes valve 42. At the same time, switch 33 supplies a signal to the third input 31 of the switch-on memory 29, which stores the switching state of switch 33 in the manner of a bistable flip circuit. This automatically switches on the current supply for the entire system, which current supply is composed of the direct voltage source 32 and the stabilizing circuit 38.

Simultaneously, the indicators of the dual-indicator manometer 23, which were blocked in the starting state, are released to return to the zero position of the manometer. More specifically, to release the indicators, switching on of the current supply excites an electromagnet which is associated with each indicator, each indicator being in the blocked state when no current is being supplied to its respective electromagnet.

Switching on of the current supply also actuates the function indicator circuit 13 and illuminates a light source belonging to this circuit. For reasons of energy savings this light source is preferably a light emitting diode. Lighting up of the light source signals that the cuff can now be pumped up by acting on the bulb 40. Since the indicators of the dual-indicator manometer 23 have been released, the manometer now indicates the pressure in the cuff, which increases with the pumping action.

Noises resulting from the pumping process, which are picked up by microphone 2 and which, after being filtered through bandpass filter 4, could erroneously be identified as Korotkoff sounds, are prevented from blocking the indicators during the pumping process by an electronic block. This electronic block is produced by a blocking signal emitted at the first output 34 of switch-on memory 29 fed to the second input 36 of the first control device 15, this signal also being fed via the second output 19 of device 15 to the second input 20 of the second control device 17. This signal blocks the first and second control devices 15 and 17 so as to prevent them from exciting the manometer electromagnets.

Once the patient has pumped the cuff to a pressure value which lies above his average systolic pressure, he switches switch 33 into the measuring position $m$ so that an automatic measuring process is initiated to measure the systolic and diastolic blood pressures.

In detail, the following takes place: Valve 42 is opened upon switching of switch 33 to position $m$ so that the air contained in the cuff can gradually escape. The pressure reduction in the cuff takes place at a speed of, for example, 5 Torr/s. Simultaneously with switching of switch 33, the above-described electronic block, which during pumping of the cuff prevented blockage of the indicators, is released.

For a certain period of, for example, 1 s, however, another block will still be effective under control of the delaying device 35. This device is preferably constituted by an RC member acting as the delaying member, whose capacitor has been charged to the potential of the blocking signal while the switch 33 was in position $p$ and discharges with its associated time constant via the associated resistor when switch 33 is switched into position $m$. The blocking signal, for example, consists of the positive, stabilized direct voltage $U_{stab}$.

The last-mentioned block has the result that the patient has some time, after switching of switch 33 into the switch position $m$, to bring the part of his body bearing the cuff into a rest position before the automatic measurement begins.

During the subsequent descent of the cuff pressure, a point is reached at which the previously stopped blood in the artery begins to flow. At this time pulsed Korotkoff sounds appear and are picked up by microphone 2 and converted into electrical oscillations. The oscillations are amplified by preamplifier 3 and, after passing through bandpass filter 4, which permits only the frequencies between 40 and 140 Hz which are characteristic for the Korotkoff sound, to pass, the oscillations are amplified further in postamplifier 5 and rectified by means of rectifier circuit 6, which is preferably a full wave rectifier. The threshold voltage of threshold value switch 7 is given a value such that only the rectified oscillations of a relatively high amplitude are converted into rectangular pulses, thereby to suppress interference.

The monostable multivibrator 8 is flipped to its quasi-stable state by the leading edge of the first pulse of the rectangular pulses and remains in that state until, for example, 300 ms have expired, at which time it flips back to its stable state. The monostable multivibrator 8 thus emits one rectangular pulse of 300 ms duration for every Korotkoff sound, which pulse acts as a blocking pulse on the function indicator circuit 13 and temporarily interrupts the light from the luminescent diode.

At the same time, the pulses from monostable multivibrator 8 arrive at the first input 14 of the first control device. A bistable flip circuit associated with the first control device takes care that only the leading edge of the first pulse from the monostable multivibrator interrupts the circuit for the electromagnet associated with the first control device 15 so that that indicator of the dual-indicator manometer 23 which is associated with this electromagnet is blocked in its present position. The indicator thus stops at a pressure value which corresponds to the systolic blood pressure.

The leading edge of the first pulse emitted by the monostable multivibrator 8 also arrives at the first input 16 of the second control device 17 to cause the flow of current in the circuit for the second electromagnet associated with the second indicator of the manometer to be halted so that the second indicator is blocked at the same time as the first indicator. The second control device 17, however, is constructed so that it excites the second electromagnet with every pulse from the monostable multivibrator 8 for the duration of that pulse so that the associated second indicator of the manometer 23 sets itself to the instantaneous cuff pressure, which drops somewhat between two successive Korotkoff sounds. Between every two pulses from the monostable multivibrator 8, the second indicator is blocked by interruption of the current flow to its electromagnet.

After the last pulse from the monostable multivibrator 8, or after the last Korotkoff noise, respectively, the second indicator of the manometer indicates the diastolic blood pressure.

Approximately 1.5 to 2 seconds after the last pulse from monostable multivibrator 8, switch-off device 27 automatically emits a switch-off pulse to switch-on memory 29, which pulse causes the current supply for the system to be switched off.

The patient can then open the outlet valve 43, and thus permit all of the air to escape from the cuff, and, finally, can remove the cuff.

The device consumes current only during the measuring process so that the battery 32 is used very sparingly.

If integrated circuits, preferably CMOS circuits, are used for the electronic portion of the apparatus, the current consumption can be kept so low that, with normal use of the system, it can be operated on one battery for more than 6 months.

Output 39 is also connected to components 3 to 8 connected to output 39 to supply their required operating voltage from circuit 38.

Figure 2:
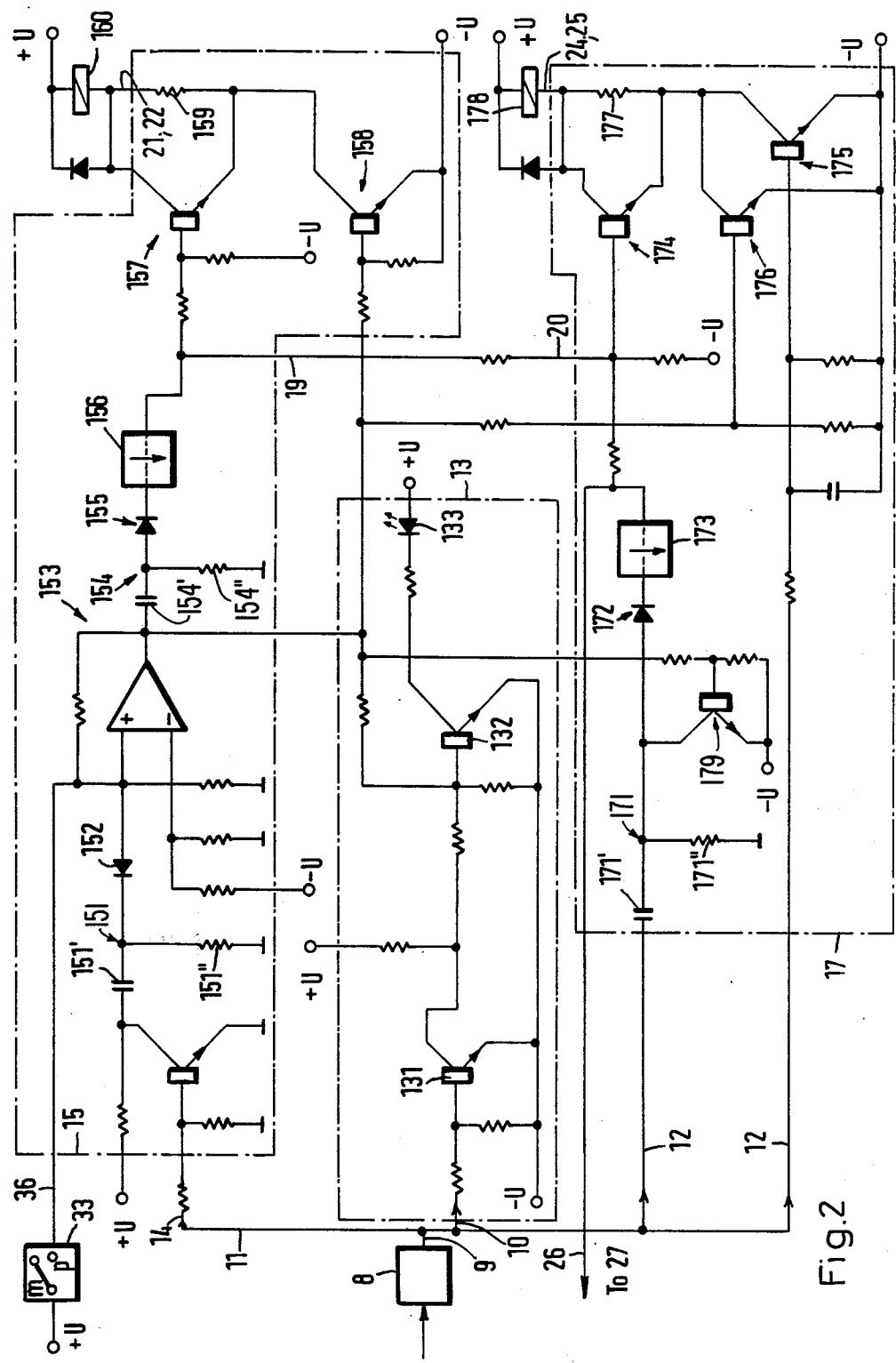
FIGS. 2 and 3 are circuit diagrams of exemplary embodiments of several of the units of the embodiment of FIG. 1.

Embodiments of units 13, 15 and 17 are shown in FIG. 2. Function indicator circuit 13 comprises two transistors 131 and 132 and a light emitting diode 133. When switch 33 is switched into its pumping position, p, the base of transistor 132 is forward-biased and diode 133 lights up. During a measurement operation, the pulses produced by monostable multivibrator 8 are fed to the transistors 131 and 132 and have the effect of periodically temporarily interrupting the light emission from diode 133.

Control device 15 consists of a first differentiation circuit 151 consisting of elements 151' and 151", a first rectifier 152, a first flip-flop 153, a second differentiation circuit 154 consisting of elements 154' and 154", a second rectifier 155, a first monostable multivibrator 156, first and second electronic switches 157 and 158, and a resistor 159. Switch 157 and resistor 159 are connected to a first solenoid 160 belonging to the manometer 23. When switch 33 is switched into its pump position, p, the positive potential + U triggers the first flip-flop 153 and the resulting output signal from that flip-flop closes switch 158. At the same time, this switching of switch 33 causes the second differentiation circuit 154 to emit a pulse spike which is passed by the second rectifier 155 and triggers the first monostable multivibrator 156 to produce an output pulse that closes switch 157, effectively short circuiting resistor 159 and thus closing an energizing circuit for the first solenoid 160. In this case solenoid 160 releases a normally blocked first pointer of the dual-indicator manometer 23 (see FIG. 1).

The control device 17 consists of a third differentiation circuit 171, consisting of 171' and 171", connected to a third rectifier 172, a second monostable multivibrator 173, third, fourth and fifth electronic switches 174, 175 and 176, and a resistor 177 with, switch 174 and resistor 177 being connected to a second solenoid 178 of manometer 23. The output of flip-flop 153 is connected to 17 thru transistor stage 179.

In the pumping position, p, of switch 33, the output signal of flip-flop 153 is simultaneously supplied to an input of the fifth electronic switch 176 which shunts the fourth electronic switch 175 and closes a circuit for the second solenoid 178. At the same time the output signal of the first monostable multivibrator 156 is supplied to the first electronic switch 174 which closes to effectively short circuit resistor 177 so that a full current can flow for energizing solenoid 178. The solenoid releases the normally blocked second pointer of manometer 23.

At the end of a selected period of time during which the monostable multivibrators 156 and 173 are triggered out of their stable state, the electronic switches 157 and 174 are opened so that only a holding current for the solenoids 160, 178 can flow.

When thereafter switch 33 is switched in its measuring position, m, the monostable multivibrator 8 emits, for each Korotkoff sound, one rectangular pulse which is led to the differentiation circuit 151, rectifier 152 and the first flip-flop 153. With the beginning of the first Korotkoff sound the flip-flop 153 emits an output signal which causes electronic switch 158 to switch to its open condition. In this condition the first pointer of manometer 23 is blocked.

During every rectangular pulse (Korotkoff sound), switch 175 is closed, causing the second solenoid 178 to release the second pointer of manometer 23. Between two consecutive pulses the second pointer is blocked.

Figure 3:
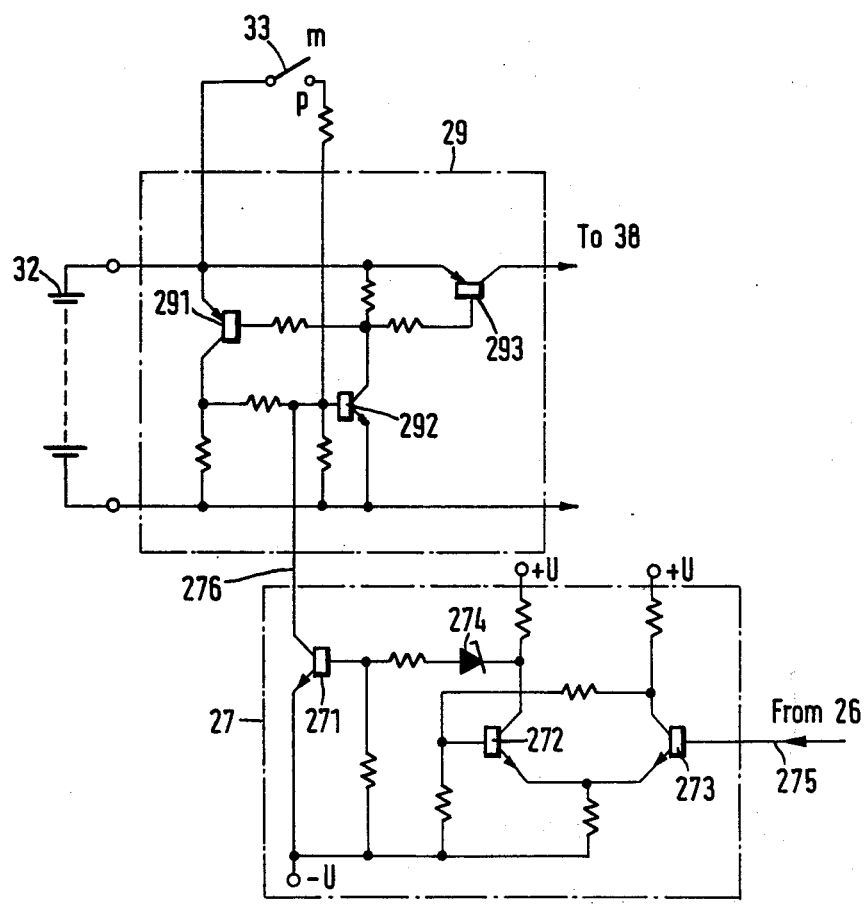

FIG. 3 illustrates an embodiment of switch-off device 27 which incudes fourth, fifth and sixth transistors 271, 272 and 273 and a diode 274, as well as an embodiment of memory 29 which includes first, second and third transistors 291, 292 and 293. The device 27 is provided with an input 275 and an output 276 which is connected with a control circuit for the second transistor 292. The third transistor 293 which is connected between a positive pole of battery 32 and the stabilization circuit 38 is controlled by a flip-flop constituted by the two transistors 291 and 292.

In their rest, or inactive, state, transistors 291 and 293 are nonconducting. In the pumping position of switch 33, the transistors 291, 292 and 293 are rendered conducting, so that the stabilization circuit 38 (FIG. 1) is conductively connected with the battery 32.

In the measuring position of switch 33, the transistor 293 remains in its conducting state. At the end of an automatic measuring procedure the second control device 17 emits at its output 26 a d.c. voltage of such value that transistor 273 becomes conducting and transistor 272 becomes nonconducting. Only in this last mentioned state do diode 274, which preferably is a Zener diode, and transistor 271 become conducting. At this time output 276 emits a negative potential, −U, to render transistors 291, 292 and 293 nonconducting, thereby disconnecting battery 32 from stabilization circuit 38.

Embodiments of units 35 and 38 are disclosed in the text, Walston and Miller, TRANSISTOR CIRCUIT DESIGN, McGraw-Hill, New York, (1963) at p. 153, FIG. 9.8 (b) and pp. 410–11, FIG. 30.2.

As unit 23 use can be made of the manometer disclosed in, and illustrated in FIG. 4 of, U.S. Pat. No. 3,056,401.

It will be understood that the above description of the present invention is susceptible to various modifications, changes and adaptations, and the same are intended to be comprehended within the meaning and range of equivalents of the appended claims.

What is claimed is:

1. A method for measuring the blood pressure of a subject according to the Riva-Rocci/Korotkoff method with an apparatus including an inflatable pressure cuff arranged to be placed in pressure-transmitting relation with an artery of the subject, manually-operable inflating means connected for inflating the cuff, a controllable valve connected for permitting the pressure in the cuff to decrease gradually, an electromechanical signal transducer arranged to be in sound-receiving communication with the artery in the region of the cuff, means for converting the electrical signals from the transducer which correspond to Korotkoff sounds into control signals, a dual-indicator manometer having first and second pressure value indicators connected to respond to the pressure in the cuff, and first and second electromagnets each associated with a respective indicator, such that excitation of an electromagnet releases its associated indicator to follow pressure variations and deexcitation of an electromagnet locks its associated indicator at its present position, control circuit means connected to the manometer for controlling the excitation of the electromagnets, electrical power supply means constituting a source of operating power for the control circuit means, and a manually operable switch connected to the valve, the control circuit and the power supply means and switchable between a pumping position in which the controllable valve is closed, the power supply means is connected to supply operating power to the control means and the electromagnets are excited, and a measuring position in which the valve is opened and the control circuit means take over control of the electromagnets, said method comprising, in the order recited;

placing the cuff in pressure-transmitting relation with the artery and the transducer in sound-receiving communication with the artery;

manually moving the switch to its pumping position;

manually operating the inflating means to inflate the cuff to a pressure above the systolic pressure of the subject;

manually moving the switch to its measuring position for causing the pressure in the cuff to gradually decrease;

automatically maintaining both electromagnets excited to enable both indicators to respond to the instantaneous pressure in the cuff until the appearance of control signals;

automatically deexciting the first electromagnet to lock the first indicator in position upon the onset of control signals;

automatically deexciting the second electromagnet to lock the second indicator in position upon the termination of control signals; and automatically disconnecting the power supply means after both electromagnets have been deexcited.

2. A method as defined in claim 1 wherein all of said manual steps are performed by the subject.

3. Apparatus for measuring the blood pressure of a subject according to the Riva-Rocci/Korotkoff method, said apparatus comprising an inflatable pressure cuff arranged to be placed in pressure-transmitting relation with an artery of the subject;

manually-operable inflating means connected for inflating said cuff;

a controllable valve connected for permitting a pressure previously established within the cuff to decrease gradually;

an electromechanical signal transducer arranged to be in sound-receiving communication with the artery in the region of said cuff when said cuff is in pressure-transmitting relation with the artery;

signal processing means connected to said transducer for converting those electrical signals from said transducer which correspond to Korotkoff sounds into control signals;

a dual indicator manometer having first and second pressure value indicators connected to respond to the pressure in said cuff, and first and second electromagnets each associated with a respective indicator in a manner that each said electromagnet, upon being excited, releases its respective indicator to follow pressure variations and, upon being deexcited, locks its respective indicator at its present position;

control circuit means connected to said signal processing means for receiving control signals therefrom and to said manometer for deexciting one of said electromagnets at the onset of a succession of control signals and deexciting the other of said electromagnets at the termination of such succession of control signals;

means defining an electronic block connected to said control circuit means and actuable to provide an output which maintains said electromagnets in their excited state;

electrical power supply means constituting a source of operating power for said control circuit means and said electronic block means, and a two-position manually operable switch operatively associated with said valve, said control circuit means, said means defining an electronic block and said power supply means and switchable between a first position in which it effects closing of said valve, supply of power from said power supply means to said control circuit means, excitation of said electromagnets and actuation of said electronic block means, and a second position in which it effects opening of said valve to permit gradual reduction of the pressure previously established in said cuff, and deactuation of said electronic block means, and permits said control circuit means to be controlled by the control signals from said signal processing means and to terminate supply of power from said power supply means when both of said electromagnets have been deexcited.

4. An arrangement as defined in claim 3 wherein said means defining an electronic block comprise a time delay member for maintaining the output provided by said means defining an electronic block for a selected time after movement of said switch from its first position to its second position.

5. An arrangement as defined in claim 3 wherein: said transducer is a microphone; said signal processing means comprise a series arrangement connected to receive the electrical signals produced by said microphone, and including at least one amplifier for amplifying those signals, a bandpass filter connected to pass those signals which correspond to Korotkoff sounds, a rectifier circuit, a threshold value circuit connected to the output of said rectifier circuit for converting only oscillations exceeding a selected amplitude into square wave pulses, and a monostable multivibrator connected to convert each pulse from said threshold value circuit into a square wave pulse of predetermined duration; and said control circuit means comprise first and second control devices each connected to receive the pulses from said multivibrator and to control a respective one of said electromagnets, and a switch-off device connected to said control devices for terminating supply of power from said power supply means.

6. An arrangement as defined in claim 5 wherein said rectifier circuit is a full wave rectifier.

7. An arrangement as defined in claim 5 wherein said microphone is mounted in said cuff.

8. An arrangement as defined in claim 3 wherein said control circuit means further comprises a function indicator device including an indicator element connected in said control circuit means to be activated to provide a detectable indication when said switch is moved to its first position and to remain activated after said switch is moved to its second position and until supply of power from said power supply means has been terminated.

9. An arrangement as defined in claim 8 wherein said indicator element is a light emitting diode.

10. An arrangement as defined in claim 3 wherein said switch includes a movable contact mechanically linked to said valve.

11. An arrangement as defined in claim 3 wherein said current supply means comprises a battery and a voltage stabilization circuit connected to the output of said battery.

12. An arrangement as defined in claim 3 wherein said control circuit means comprises a memory connected to provide a signal representing the present position of said switch.

13. An arrangement as defined in claim 3 wherein said signal processing means, control circuit means and electronic block defining means are constituted by integrated circuits.

14. An arrangement as defined in claim 13 wherein said integrated circuits are CMOS circuits.

* * * * *